United States Patent
Govinahallisathyanarayana et al.

(10) Patent No.: US 11,382,596 B2
(45) Date of Patent: *Jul. 12, 2022

(54) METHOD FOR ALIGNING SPATIALLY DIFFERENT SUBVOLUMES OF ULTRASONIC DATA OF A BLOOD VESSEL

(71) Applicant: KONINKLIJKE PHILIPS N.V., Eindhoven (NL)

(72) Inventors: Sushanth Govinahallisathyanarayana, Bangalore (IN); Rajendra Singh Sisodia, Bangalore (IN); Nagaraju Bussa, Bangalore (IN); Krishnamoorthy Palanisamy, Bangalore (IN); Vikram Basawaraj Patil Okaly, Bangalore (IN); Shriram Sethuraman, Briarcliff Manor, NY (US); John Petruzzello, Carmel, NY (US); Shiwei Zhou, Yorktown Heights, NY (US); Ajay Anand, Fishkill, NY (US); Ramon Quido Erkamp, Yorktown Heights, NY (US); Shankar Mosur Venkatesan, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 958 days.

This patent is subject to a terminal disclaimer.

(21) Appl. No.: 14/906,611

(22) PCT Filed: Jul. 14, 2014

(86) PCT No.: PCT/IB2014/063077
§ 371 (c)(1),
(2) Date: Jan. 21, 2016

(87) PCT Pub. No.: WO2015/011599
PCT Pub. Date: Jan. 29, 2015

(65) Prior Publication Data
US 2016/0151038 A1 Jun. 2, 2016

Related U.S. Application Data

(60) Provisional application No. 61/857,833, filed on Jul. 24, 2013.

(51) Int. Cl.
*A61B 8/06* (2006.01)
*A61B 8/08* (2006.01)
(Continued)

(52) U.S. Cl.
CPC .............. *A61B 8/06* (2013.01); *A61B 8/0891* (2013.01); *A61B 8/466* (2013.01); *A61B 8/483* (2013.01);
(Continued)

(58) Field of Classification Search
CPC ......... A61B 8/06; A61B 8/0891; A61B 8/466; A61B 8/483; A61B 8/488; G01S 7/52065;
(Continued)

(56) References Cited

U.S. PATENT DOCUMENTS 4,202,215 A * 5/1980 Meyer .................... G01N 29/11
73/599
5,474,073 A * 12/1995 Schwartz ............ G01S 15/8979
600/456
(Continued)

FOREIGN PATENT DOCUMENTS

JP 2009131420 A 6/2009
WO 200072756 A1 12/2000
(Continued)

OTHER PUBLICATIONS

Krucker, Jochen F. et al "Rapid Elastic Image Registration for 3-D Ultrasound" IEEE Transactions on Medical Imaging, vol. 21, No. 11, Nov. 2002.

(Continued)

*Primary Examiner* — Luther Behringer
*Assistant Examiner* — Amy J Shafqat (57) ABSTRACT

A method for aligning spatially different subvolumes of ultrasonic data of a blood vessel comprising: acquiring temporally discrete signals of a blood vessel with elements of a two dimensional array of ultrasonic transducer elements from spatially different depths of scanning opposed by each transducer element, said array being located in a first position with respect to the blood vessel during the acquiring; Doppler processing the temporally discrete signals received from each transducer element to produce spectral Doppler data of the scanning depth opposed by each transducer element; producing a first three dimensional map of the spectral Doppler data in spatial relationship to the position of the array with respect to the blood vessel; acquiring temporally discrete signals of the blood vessel with elements of the two dimensional array of ultrasonic transducer elements from spatially different depths of scanning opposed by each transducer element, said array being located in a second position with respect to the blood vessel during the acquiring; Doppler processing the temporally discrete signals received from each transducer element to produce spectral Doppler data of the scanning depth opposed by each transducer element; producing a second three dimensional map of the spectral Doppler data in spatial relationship to the position of the array with respect to the blood vessel; aligning the first three dimensional map with the second three dimensional map on the basis of one or more regions of matching spectral Doppler data of the two map; and producing a combined three dimension map of the blood flow of the vessel from the aligned first and second three dimensional maps.

13 Claims, 7 Drawing Sheets

(51) Int. Cl.
  *G01S 7/52* (2006.01)
  *A61B 8/00* (2006.01)
  *G01S 15/89* (2006.01)
(52) U.S. Cl.
  CPC .......... *A61B 8/488* (2013.01); *G01S 7/52065* (2013.01); *G01S 15/8979* (2013.01); *G01S 15/8925* (2013.01); *G01S 15/8993* (2013.01)
(58) Field of Classification Search
  CPC ............. G01S 15/8979; G01S 15/8925; G01S 15/8993
  See application file for complete search history.

(56) References Cited

U.S. PATENT DOCUMENTS

| | | | |
|---|---|---|---|
| 6,682,483 B1 | 1/2004 | Abend | |
| 7,347,820 B2 | 3/2008 | Bonnefous | |
| 7,529,393 B2 | 5/2009 | Peszynski | |
| 9,351,708 B2 | 5/2016 | Anand | |
| 2003/0013958 A1* | 1/2003 | Govari | G01S 7/5208 600/437 |
| 2003/0163046 A1* | 8/2003 | Nohara | G01S 15/8993 600/443 |
| 2004/0019278 A1* | 1/2004 | Abend | G01S 7/52026 600/454 |
| 2004/0267127 A1* | 12/2004 | Abend | A61B 8/06 600/450 |
| 2008/0183077 A1* | 7/2008 | Moreau-Gobard | A61N 7/02 600/439 |
| 2008/0281206 A1 | 11/2008 | Bartlett | |
| 2009/0003675 A1* | 1/2009 | Moreau-Gobard | A61B 5/6804 382/131 |
| 2009/0024034 A1* | 1/2009 | Moreau-Gobard | A61B 8/4227 600/443 |
| 2009/0067699 A1 | 3/2009 | Clark | |
| 2009/0112095 A1* | 4/2009 | Daigle | A61B 8/5223 600/454 |
| 2011/0109650 A1* | 5/2011 | Kreeger | G16H 50/50 345/634 |
| 2011/0125022 A1* | 5/2011 | Lazebnik | A61B 8/4461 600/444 |
| 2011/0196237 A1* | 8/2011 | Pelissier | A61B 8/06 600/454 |
| 2012/0184854 A1 | 7/2012 | Raju | |
| 2013/0225994 A1* | 8/2013 | Hsu | A61B 8/08 600/439 |
| 2014/0228688 A1* | 8/2014 | Gupta | A61B 8/06 600/454 |
| 2014/0285623 A1* | 9/2014 | Bruls | G06T 5/002 348/43 |
| 2014/0358000 A1* | 12/2014 | Gupta | A61B 8/06 600/441 |
| 2016/0157814 A1* | 6/2016 | Palanisamy | A61B 8/06 600/454 |

FOREIGN PATENT DOCUMENTS

| | | |
|---|---|---|
| WO | WO2011027253 A1 | 3/2011 |
| WO | 2013088320 A1 | 6/2013 |

OTHER PUBLICATIONS

Meyer, Charles R. et al "Semiautomatic Registration of Volumetric Ultrasound Scans", Ultrasound in Medicine and Biology, vol. 25, No. 3, 1999, pp. 339-347.

* cited by examiner

Laminar flow          Turbulant flow

FIG. 8

- Generate spectrogram from Doppler signal → Spectrogram from Doppler signal
- Extract the upper and lower trace from the spectrogram → Extract upper and lower spectral trace
- (area under upper trace − area under lower trace) / area under upper trace → Evaluate difference between areas under upper and lower trace in proportion to area under upper trace

METHOD FOR ALIGNING SPATIALLY DIFFERENT SUBVOLUMES OF ULTRASONIC DATA OF A BLOOD VESSEL

CROSS-REFERENCE TO PRIOR APPLICATIONS

This application is the U.S. National Phase application under 35 U.S.C. § 371 of International Application No. PCT/IB2014/063077, filed on Jul. 14, 2014, which claims the benefit of U.S. 61/857,833, filed on Jul. 24, 2013. These applications are hereby incorporated by reference herein.

This invention relates to medical diagnostic ultrasound systems and, in particular, to a non-imaging Doppler probe system for automated screening of carotid stenosis.

Stroke is the third leading cause of death world-wide. According to the World Health Organization, stroke accounted for more than 5.5 million deaths in 2002 with about 50% of those deaths occurring in China and India. Although the incidence is declining in developed countries, stroke nevertheless accounts for a mortality of 163,000 in the United States. A significant portion of these deaths are believed to be a result of disease in the carotid bifurcation. The carotid artery bifurcation, where the common carotid artery (CCA) branches into the internal (ICA) and external (ECA) carotid arteries, is a common site of atherosclerotic disease. Stenosis or narrowing of the ICA, the branch which supplies blood to the brain, has long been known to be related to the incidence of ischemic stroke. The use of the severity of carotid stenosis has evolved as a surrogate measure of the risk of stroke.

The incidence of carotid atherosclerosis and mortality associated with stroke is an increasing problem in the developing world. In these countries, a carotid artery screening device that can be used in low resource settings would address this growing problem by offering several features. First, there is often a lack of skilled personnel in these settings, and so the device should be able to be used with minimal training and instruction. Second, the device should be inexpensive so as to be affordable in these settings. Third, the device should be able to classify the degree of stenosis in the carotid arteries in a highly automated way without the use of high-end duplex ultrasound scanners that may not be available in the rural setting.

In accordance with the principles of the present invention, a diagnostic ultrasound system for carotid artery diagnosis includes a simple, non-imaging Doppler ultrasound probe. The probe has a two dimensional array of transducer elements with a low count of elements of relatively large size which can cover an area of the carotid artery at its bifurcation. The large sized elements are operated independently with no phasing, thereby reducing the cost of the Doppler system. The probe and system of the present invention can produce a representation of carotid blood flow in two or three dimensions and can assemble an extended view of the flow by matching segments of the carotid flow as the probe is moved over the vessel. Once the carotid artery has been localized, the degree of stenosis is assessed by automated measurements of peak systolic velocity and blood flow turbulence.

Figure 1:
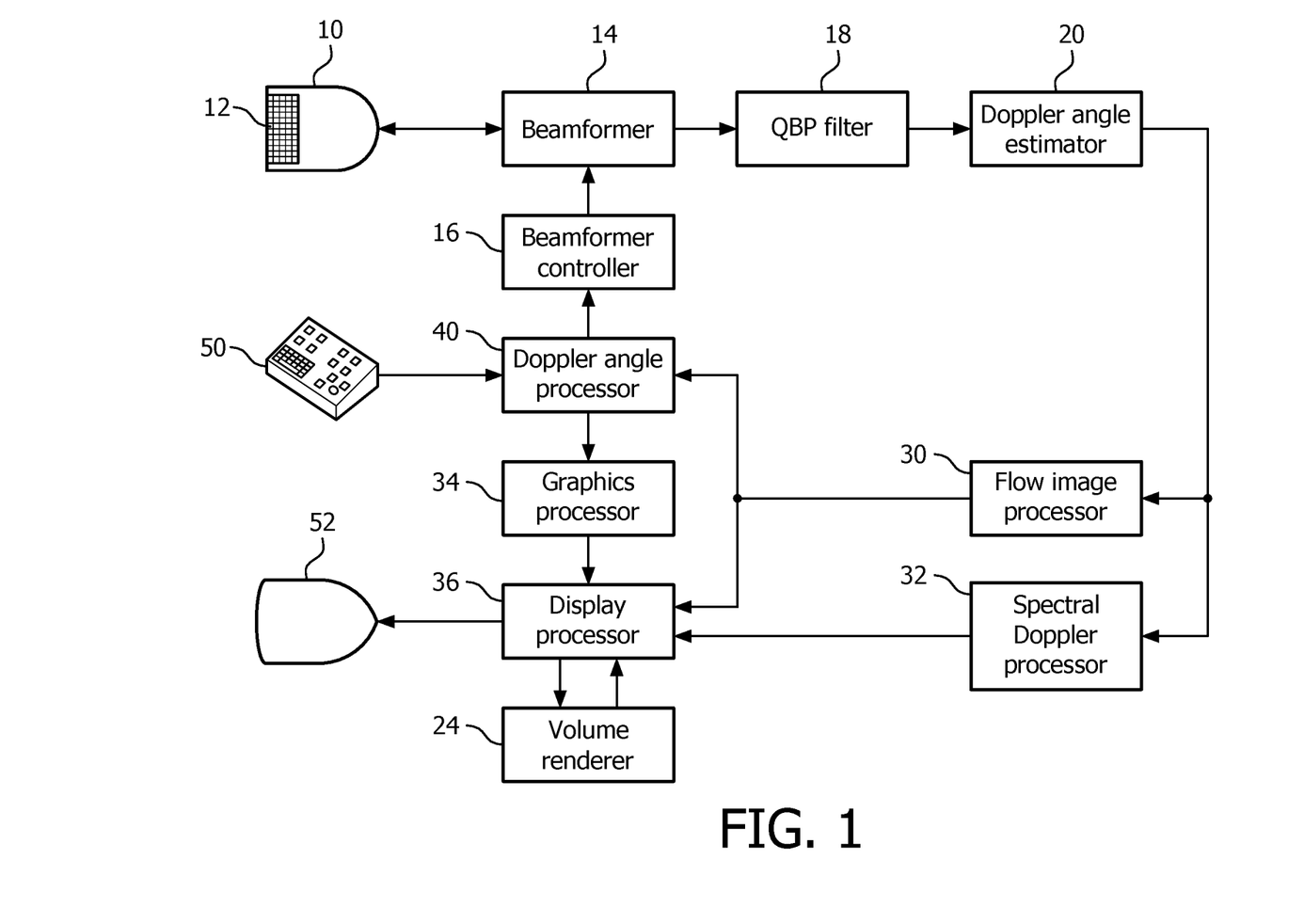
FIG. 1 illustrates in block diagram form an ultrasound system constructed in accordance with the principles of the present invention.

Referring first to FIG. 1, an ultrasound system constructed in accordance with the principles of the present invention is shown in block diagram form. An ultrasound probe 10 contains a transducer array 12 of transducer elements which transmit ultrasound waves into the body and receive returning echo signals for Doppler processing. Control and timing of ultrasound transmission and reception is provided by a beamformer controller 16 which controls system beamformer 14. The beamformer 14 is not a conventional delay-and-sum beamformer as the transducer array is not operated in a phased manner. Instead, each element is separately actuated to transmit ultrasound waves directly into the body from its front surface and receive reflections from the waves individually. The beamformer controls the timing of successive transmit-receive intervals (the pulse repetition interval or PRI) by each transducer so that an ensemble of temporally spaced echoes is received by each transducer element at successive depths over a depth range of interest, which is the nominal depth at which the carotid artery is located. Each ensemble of echo samples can then be Doppler-processed to detect the flow condition in front of every transducer element. A quadrature bandpass filter 18 processes the echo signals into quadrature I and Q components. The separate components are used by a Doppler angle estimator 20 to estimate the phase or frequency shift of a Doppler signal at the depths in front of each transducer element where Doppler interrogation is to be performed. Alternatively Doppler power may be estimated. The Doppler frequencies or intensities at depths in front of each transducer which are produced by the Doppler angle estimator 20 can be mapped directly to velocity values of flow or Doppler power at those depth locations. This Doppler data is coupled to a flow image processor 30 which spatially processes the data into a two or three dimensional image format, in which the velocity values are color- or intensity-coded. This spatial Doppler vessel map is processed by a display processor 36 and displayed on display 52 to illustrate the locations in the anatomy beneath the array transducer where flow is taking place and the velocity and direction of that flow by the color coding or Doppler power by intensity modulation. Doppler data is also coupled to a spectral Doppler processor 32 which produces a spectral analysis of the Doppler data for peak systolic velocity and turbulence analysis as described below. A Doppler angle processor 40 conditions the process for the angle of Doppler interrogation which is preferably set by inclining the direction of wave transmission by the transducer elements as described below. A graphics processor 34 is provided to overlay vessel map coordinates and other graphical data such as patient name on the displayed image. A volume renderer 24 performs volume rendering of three dimensional vessel map data for the production of three dimensional vessel maps as described below. The entire system is operated by user controls 50.

Figure 2:
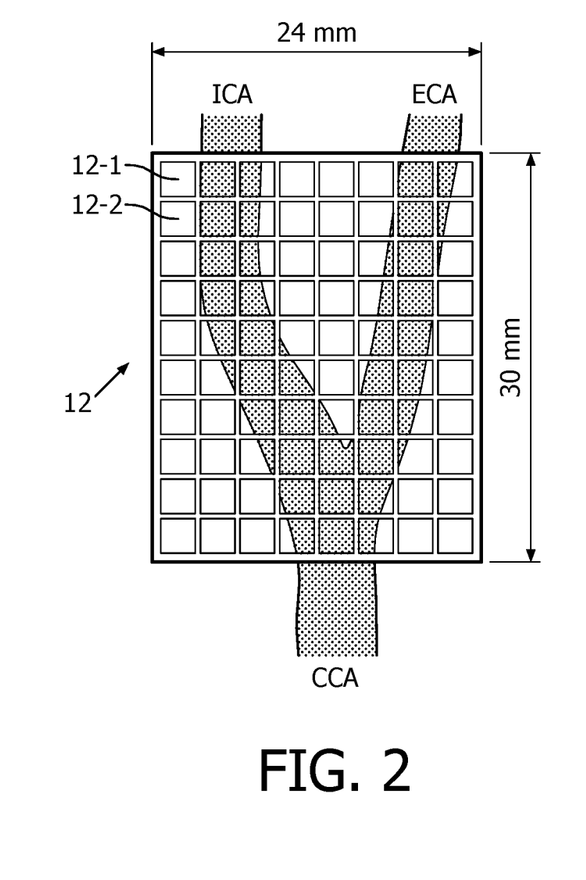
FIG. 2 illustrates the size and dimensions of the elements of an array transducer of a probe of the present invention.
Figure 2A:
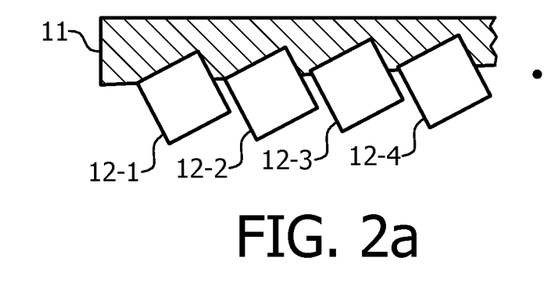
FIG. 2a illustrates the angling of the transducer elements of the array of FIG. 2 for good Doppler reception.

FIG. 2 illustrates a transducer array 12 for a probe 10 of the present invention. This embodiment is an array for a probe with a total of 80 elements, each measuring 3 mm by 3 mm arranged in a two dimensional matrix containing 10 rows by 8 columns. In such a configuration, the area of coverage is 30 mm by 24 mm. Transducer arrays with this small number of elements and elements of this relatively large individual size are easier to dice than fine-pitched array elements, making this array simple to fabricate with high yields and hence relatively inexpensive to make. The factors to consider in selecting the number of element include coverage, resolution, and a number which provides acceptable accuracy as compared to a standard ultrasound probe. Element sizes ranging from 3 mm by 3 mm to 6 mm by 6 mm have been found to be acceptable for unfocused elements used with nominal depths of the carotid artery. An array size of around 40 mm has been found suitable for covering the branches of the carotid artery. As FIG. 2 illustrates, the probe is intended to be placed against the neck of a patient over the carotid artery. When the probe aperture is longitudinally in line with the carotid artery and the bifurcation of the artery is within the field of view, the transducer will cover an appreciable area of the carotid artery with the common carotid artery (CCA) at one end and the internal (ICA) and external (ECA) branches at the other end. The elements in the probe are placed at an angle to provide a Doppler angle of 30-60 degrees. As is well known, no Doppler signal can be obtained when the direction of blood flow is orthogonal to the direction of the ultrasound waves, and maximal signals are obtained when the wave are directed in line with the flow. Thus, if the elements of the array 12 were aimed straight into the body, little or no Doppler signals would be realized from the carotid flow immediately beneath the array. To account for this directional sensitivity the elements of the array 12 are angled at an angle of 30-60 degrees away from normal as illustrated in FIG. 2*a*. A tilt of around 30 degrees has been found to yield acceptable results. Additional angulation can be provided by tilting the probe in relation to the skin surface during scanning. This drawing shows the end elements 12-1, 12-2, 12-3 and 12-4 of the first four rows of elements canted at the selected Doppler angle and retained in position by an overlying layer of transducer lens material layer 11 which is generally a polymeric rubber-like material such as RTV. The thickness of the RTV lens can be uniform across the array transducer, or can be tapered in thickness to provide some or all of the tilt for setting the nominal Doppler angle. The Doppler angle at which the elements are angled can be entered into the ultrasound system automatically from the probe's personality chip or manually from the user controls to condition the system to account for the proper angle correction to be used for the Doppler angle of the probe elements. The system may desirably also include a Doppler angle feedback indicator controlled by an algorithm that processes the strength of the Doppler return signals and detects unfavorable Doppler angles, which suggests that the user manually reposition the probe at a more favorable angle.

The elements of the array transducer are excited with excitation pulses to work in the pulsed wave mode. In the pulsed wave mode, it is possible to provide depth resolution of the Doppler signals. For instance, an element size of 3 mm by 3 mm generally provides enough resolution to sample and obtain the velocity in a narrow region of the high speed jet produced in carotid arteries with stenosis. The elements of the non-phased transducer array 12 are fired simultaneously or independently in a customizable firing sequence under control by the beamformer 14.

Figure 4:
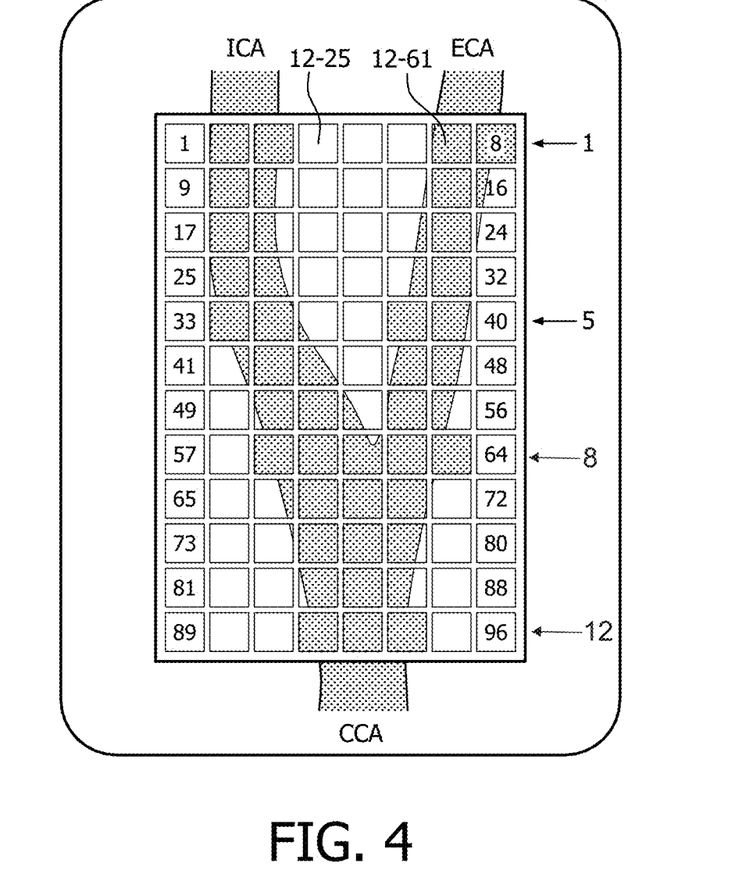
FIG. 4 illustrates the operation of a Doppler probe of the present invention in discrete rows of elements.
Figure 5:
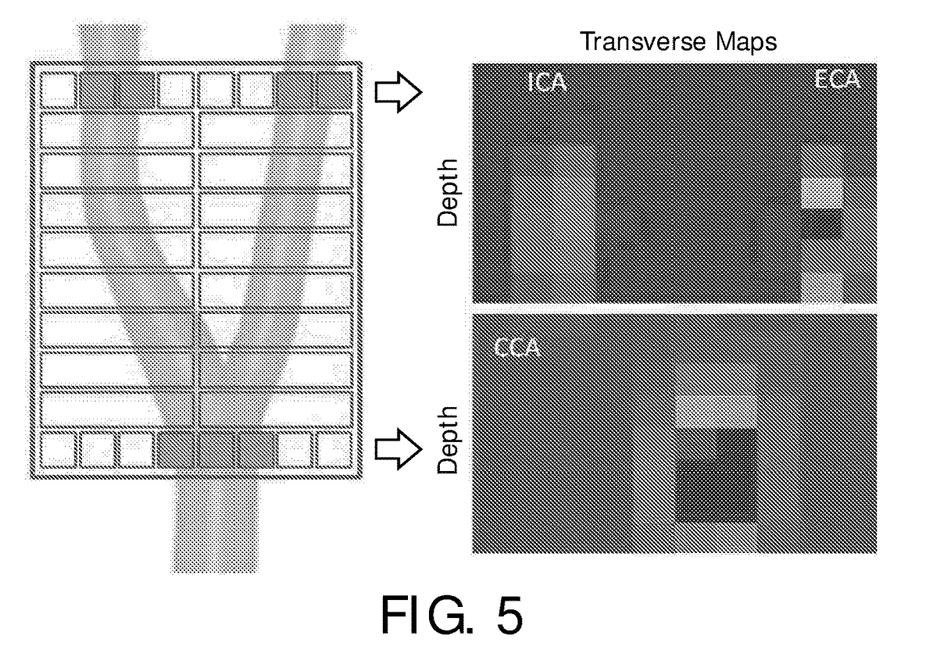
FIG. 5 illustrates a two dimensional vessel map produced by an ultrasound system of the present invention.

Operation of a probe and system of the present invention proceeds as follows. A sequence of elements (a small sub-section of the entire probe) is fired simultaneously. The sample volume for Doppler flow interrogation in front of each element is increased sequentially to cover a range of depths. In the embodiment of FIG. 4, in which the probe contains an array of 96 elements, 4 rows could be activated simultaneously, e.g., rows #1, #5, #8 and #12 as shown in this drawing. The Doppler spectrum is acquired continuously from each of the 8 elements in each of these rows. After at least 3 cycles of Doppler flow data are acquired, the flow image processor 30 computes a sum-plot (integration of Doppler power in a specified frequency band, e.g. 300 Hz to 1500 Hz). The magnitudes of the sum-plot values enable the elements that are directly above the vessel to be identified. For instance, transducer element 12-25 is not over a portion of the carotid artery and will sense no flow (will produce a negligible power Doppler signal.) Transducer element 12-61, on the other hand, is directly above the carotid artery and will produce a significant power Doppler signal. The flow image processor 30 can then produce a grid-like map of the location and position of the carotid artery branches beneath the probe as indicated in FIGS. 4 and 5. Each box in an 8 by 12 display grid is filled in with a brightness or color when a significant Doppler signal is detected by a corresponding transducer element, and is not illuminated when substantially no Doppler signal is detected. In FIG. 4, for instance, the third, fourth, seventh and eighth boxes in the first row of the grid are illuminated in response to the detection of flow in the ICA and ECA by those elements in that row which are over those carotid branches. A similar result is obtained from elements 34, 35, 38 and 39 in row 5. Boxes corresponding to elements 59-63 of row 8 are illuminated because they detected flow in the CCA below the carotid bifurcation, as is also the case for boxes corresponding to elements 92-94 in row 12. As FIG. 4 illustrates, this will present a simple two dimensional grid vessel map of the flow in the carotid artery beneath the array transducer. A similar result can also be obtained in the depth dimension as shown in FIG. 5. This shows the results from depth-gating the Doppler signal samples from six discrete depths below the elements in the top and bottom rows of the array 12. The transverse maps to the right of the array illustration shows faintly illuminated blocks at six depths where the second, third, seventh and eighth elements in the top row have detected flow in the ICA and the ECA. The lower map shows a wider, more illuminated set of depth blocks where the center three elements of the bottom row of elements have detected the stronger flow in the CCA which is beneath that row of elements. The values of these vertical depth block in each column can be combined in various ways to obtain a display value for a box in the longitudinal display shown to the left of the transverse maps, if desired.

Figure 3:
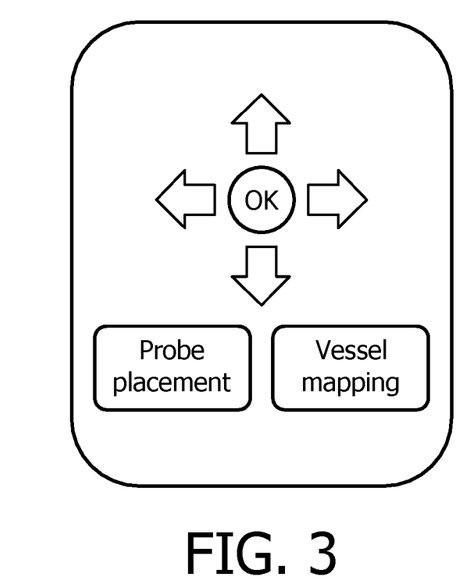
FIG. 3 illustrates a probe placement display of an ultrasound system of the present invention which guides an operator in proper probe placement over the carotid artery.

An object of an implementation of the present invention is to provide real-time feedback to the user such that the user is guided in placing the probe on the neck so that it covers the bifurcation of the carotid artery. Since this is a non-image based system, feedback can be given to the user through a set of indicators on the screen that guides the user to move the probe in the appropriate direction. In this example, the ideal placement of the probe is when the flow image detector detects a single vessel branch (CCA) at rows 8 & 12 of the grid display and two separate vessel branches (ICA and ECA) in rows 1 & 5 of the grid as shown in FIG. 4. The elements in these rows are continuously fired and the flow image processor computes the accumulated Doppler power of the signals received by each element in real time. The grid blocks which are illuminated in response to significant Doppler signal returns inform the system of the placement adjustment needed to obtain good probe placement. If the placement is good, the "OK" indicator is highlighted in the probe guidance display of FIG. 3. If not, appropriate one of the arrows in the guidance display are highlighted to guide the user in probe placement. An optimal positioning of the probe is achieved when the display grid showing the depth accumulated Doppler power (FIG. 4) indicates a separation of the vessel segments in the carotid bifurcation. The "Probe placement" and "Vessel Mapping" display buttons at the bottom of the guidance display tell the user the current mode of operation, either probe placement or vessel mapping. If the user is in the Vessel Mapping mode and wants to readjust the positioning of the probe over the carotid artery, the user taps the Probe placement display button to return the system to that mode and the Probe placement button responds by illuminating. Since approximately 3 seconds worth of Doppler data is required for a single iteration, a guidance indication can be determined and updated in a time of 3 seconds. The maximum time to achieve acceptable placement of the probe over the carotid artery depends on the number of iterations required to successfully place the probe in the proper position for carotid artery stenosis detection.

Figure 6:
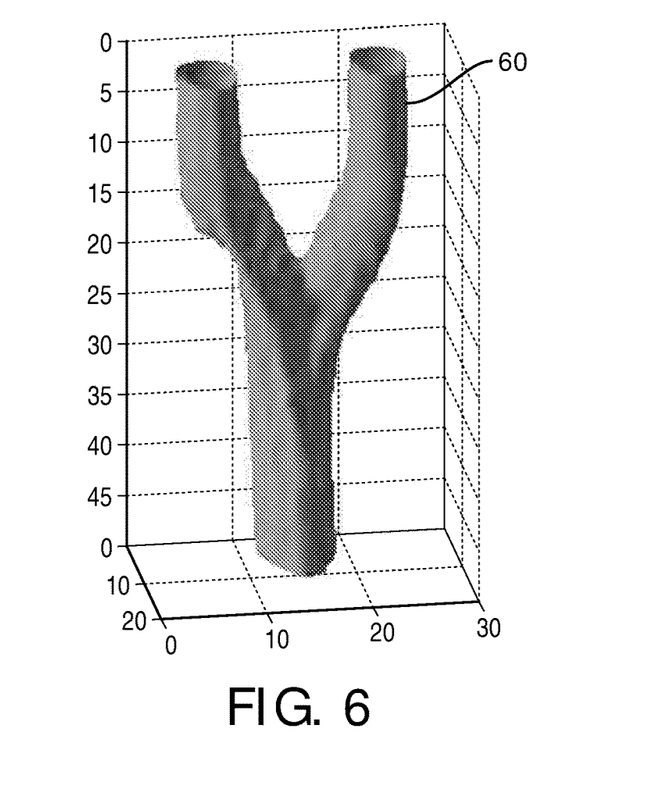
FIG. 6 illustrates a three dimensional vessel map produced by an ultrasound system of the present invention.

Once the probe is placed, the next step is to obtain ultrasound Doppler data from all the elements in the probe array and map the vessels in accordance with the elements which detect flow. The accumulated Doppler power is computed as described above in conjunction with FIG. 5 for the depths of interest to generate a 3D representation of the carotid vessels. The 3D representation is produced from the depth values detected by all of the elements and processed by the volume renderer 24 into a 3D display map. As shown in FIG. 6, a 3D display map 60 of the bifurcated vessel is displayed.

Following vessel mapping in either two (FIG. 4) or three (FIG. 6) dimensions, Doppler data is acquired from all of the elements to extract the peak systolic velocity which can aid in classification of a stenosis. Additionally if desired a Doppler spectrum can be extracted at a suspected point of stenosis to further aid the diagnosis as described below.

When the probe 10 has a small aperture, it may not be possible to acquire a sufficiently sized portion of the carotid, its branches and bifurcation in a single acquisition. In such a case multiple volume acquisition is employed to acquire segments of the carotid artery in sub-areas or sub-volumes by movement of the probe along the neck, then stitching the smaller segments together to form the desired vessel map. Manual movement of probe implies that there is no calibration, the overlap region may vary among two consecutive acquisitions, and there is also potential variation in the angle and quality of signal acquisition. Thus, instead of all the data being acquired in one volume, data is acquired in multiple sub-volumes to cover the entire carotid anatomy. From the multiple acquisitions, the carotid vascular anatomy must be reconstructed to verify if the entire carotid anatomy was scanned, and so the sub-volumes must be stitched together. This is done by "stitching" together successively acquired, spatially different but overlapping subvolumes by aligning their matching data in the overlapping region. The overlapping region of each subvolume is determined from a match of the time domain Doppler obtained from the individual transducer elements. As a simple example, one subvolume may have a column of voxels with flow velocity values of 0, 3, 5, 3, and 0 cm/sec. When a matching column of voxels in an overlapping subvolume is found with the same or similar Doppler values, the subvolumes are aligned on the basis of this identity of sequential voxel values. Other Doppler spectral characteristic instead of or in addition to velocity can be used to make the match. This stitching is performed purely based on the signal characteristics because relative position of the probe with reference to the neck is not easy to obtain.

Accurate vessel stitching is essential in order to reconstruct the vascular anatomy to estimate the angle of insonation across multiple volumes at one sweep of the probe. This enables the determination of peak systolic velocity across the anatomy. Peak systolic velocity is a clinically accepted diagnostic indicator to grade stenosis according to the following consensus criteria:

| Degree of stenosis | PSV (cm/s) |
| --- | --- |
| Normal or <50% | <125 |
| 50%-69% | 125-230 |
| >70% | >230 |
| Total occlusion | No flow |

Figure 7A:
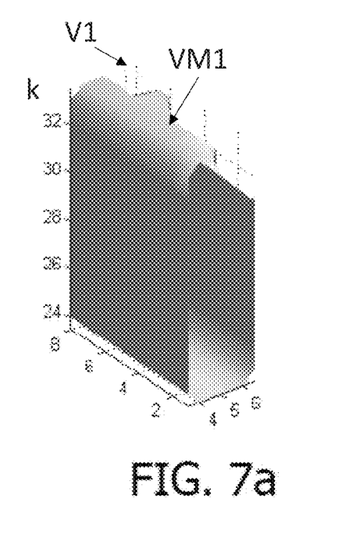
FIGS. 7a-d illustrate the progressive assembly of a three dimensional vessel map produce by scanning with a probe and system of the present invention.
Figure 7B:
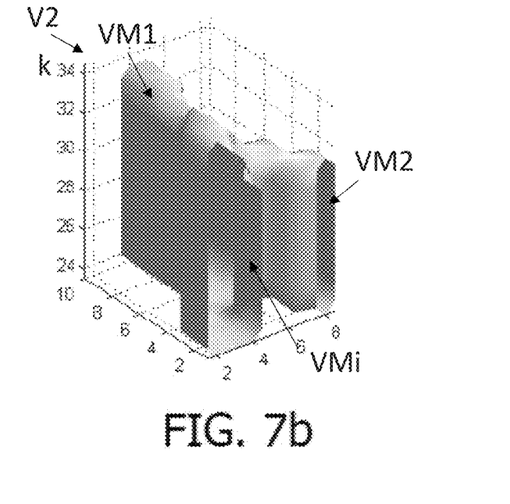
Figure 7C:
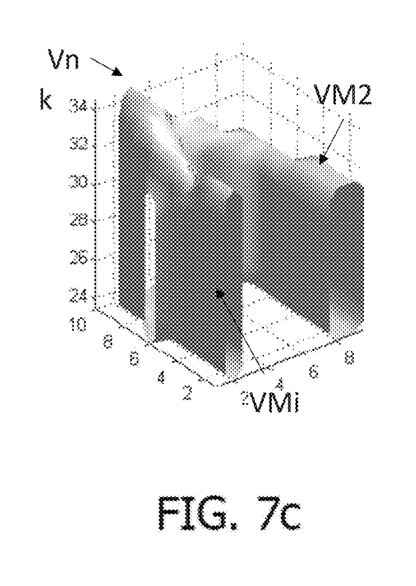
Figure 7D:
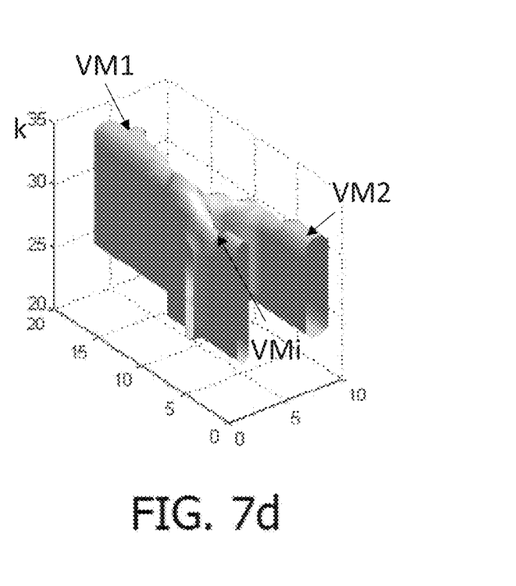

Since the probe 10 is non imaging, it is difficult for the user to understand how much of the artery cluster under investigation has been covered by a sweep of the probe. It is difficult to interpret from the reconstruction of any of the typical sampled sub-volumes, e.g., V1, V2, or Vn of FIG. 7(*a*), 7(*b*), or 7(*c*), respectively, whether the artery structure has been covered with anatomical cues from a single volume. Therefore, the data from multiple volumes is stitched together to completely reconstruct the vascular anatomy and provide an anatomical basis for artery identification. Anatomical cues from the generated vessel map of the sub-volumes are used as well as signal characteristics to complete the vascular anatomy reconstruction. When the Doppler signal is of sufficient signal to noise ratio to obtain a complete anatomical reconstruction in pulsatile flow, and the probe is moved uniformly over the artery structure under investigation, the following steps may be employed in accordance with the present invention to reconstruct the full anatomy. First, the probe 10 is placed in a first location resulting in acquisition of sample volume V1. The probe is manually moved to a second location, adjacent to the first location such that the resulting new acquisition sample volume V2 is partially overlapped with V1. Each volume in this example is a three dimensional matrix containing returned ultrasound echo data. Next, further sample volumes Vn are acquired in the same manner, such that the vessel structure of interest is fully covered. Since this is a non-imaging approach, it may not be feasible to know the completion of vessel map reconstruction until the end of the process.

Next, for each of the volumes V1 through Vn, signal in the volume is identified by highlighting the different segments in the 3D space of the vessel as shown in FIG. 7. Vessel map identification is used to identify a vessel segment in a given volume. Let VM=a list of unique vessel segments (VM1-VMi) identified using the previous step. The number of vessel segments VM, is compared among the sample volumes. This helps to clearly identify the region of overlap in the sample volume where the number of regions is non uniform, such as the volume containing the bifurcation point of the carotid artery, using anatomical information from the reconstruction. It also gives an indication of where to search for matching signal data, e.g., the overlap between FIG. 7(b) and FIG. 7(c) can only be where there are two distinct vessels VM2 and VMi in FIG. 7(b).

The data of all the good spectra from the top most row of each column of one sample volume is extracted in order, and correlated with the data of each of the rows of the subsequent (adjacent) volume. A spike in correlation at row k indicates that all the data from row k to the last row of the probe are in the overlapping region. Since the effects of noise are unpredictable on the signal, it may happen that one of the acquisitions of the overlapping volumes is more contaminated by noise than the other. In this case, the overlapping area is assigned to the volume where this area has more analyzable spectra. In the event that the number of such spectra is equal, the overlapping region can be assigned to either volume.

Let there be p rows matching the anatomical cues (or number of regions in the slice). Let the signals of each transducer on these p rows at all depths showing pulsatile flow (signal from blood flow) be $T_{ij}$. Let the pulsatile signal of the ith row of transducers be $R_i$:

$$R_i = \Sigma_{j=1}^{c} T_{ij} \quad \text{(i)}$$

where c is the number of columns. The matrix of row signals RM is obtained as:

$$RM = [R_1 \, R_2 \, R_3 \ldots R_k \ldots R_p] \quad \text{(ii)}$$

Let the signal on the first row of the previous volume be FS:

$$FS = \Sigma_{j=1}^{c} T_{1j} \quad \text{(iii)}$$

where c is the number of columns. The start of the overlap region is obtained by cross-correlating the row signal matrix with FS as follows:

$$CV = \text{CrossCorr}(RM, FS)$$

$$CV = \Sigma_{n=-inf}^{inf} RM(i+n)\cdot FS(k) \quad \text{(iv)}$$

Where $$RM(i+k) \text{ is } \begin{bmatrix} R_1(i+k) \\ R_2(i+k) \\ R_3(i+k) \\ \ldots \\ R_p(i+k) \end{bmatrix}$$

CV is the vector of cross correlations $$k = \text{Max}(|(CV)|) \quad \text{(v)}$$

and $R_k$ is the row corresponding to index k. Since the direction of motion is assumed to be uniform and correlation is performed to find the start of the overlapping region we know that $R_k$ to $R_p$ is the overlapping region. Volume data from $R_k$ to $R_p$ is assigned to the corresponding volume. This yields the volumes to be stitched as $S_1$, $S_2$ and $S_3$. The volumes to be stitched are stacked in the direction of motion and connected by interpolation and/or smoothing.

Figure 8:
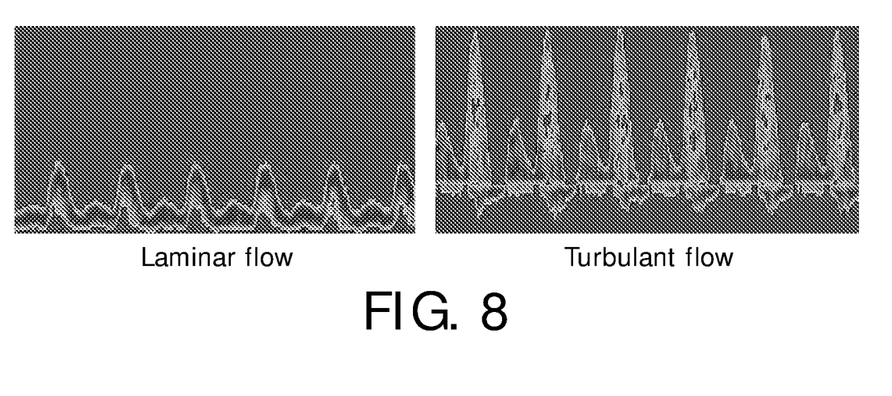
FIG. 8 illustrates spectral Doppler displays of flow conditions encountered in the carotid artery.

Blood flow in the carotid artery can be laminar or turbulent. Laminar flow is uniform, with all blood cells moving at relatively the same speed and in the same direction. Turbulent flow is characterized by random chaotic swirling, in which blood cells within the vessel are moving in many directions but typically have a net forward flow. Doppler spectra of laminar flow appear as broadening of the spectral line and filling of the spectral window. A turbulent flow pattern appears as spectral broadening with components below the baseline. Spectral broadening is a term applied to waveform alterations that are representative of turbulent flow. It is defined as the increased distribution of the frequencies present in a Doppler spectrum as illustrated by the Doppler flow spectrograms of FIG. 8. In the carotid artery, this type of turbulence is present at the bifurcation point (i.e., the carotid bulb, equivalent from the point of view of flow characteristics) and at a narrowing or stenosis of the vessel.

The main way of distinguishing these two cases of turbulence is through the measurement of the peak systolic velocity (PSV). The presence of stenosis is usually characterized by an elevated PSV accompanying turbulence. The criteria for dangerous levels of plaque are generally related to percentage of stenosis; also, the degree of stenosis is determined by the peak velocity of the blood as follows:

| Degree of stenosis | PSV (cm/s) | Turbulence (Spectral Broadening) |
|---|---|---|
| Normal | <125 | Normal & High at carotid bulb |
| <50% | <125 | High |
| 50%-69% | 125-230 | High |
| >70% | >230 | High |
| Total occlusion | No flow | Nil |

Detecting the Doppler shift caused by increased velocity can determine whether there is dangerous plaque present.

Distinguishing the characteristics of the bifurcation of the carotid artery from the characteristics of a stenosis can be done as follows:

| Condition/Feature | PSV | Turbulence (Spectral Broadening) |
|---|---|---|
| Bifurcations (Carotid bulb) | Normal | High |
| Stenosis | High | High |

This relationship shows that by estimating the turbulence in terms of spectral broadening and the PSV one can easily identify the segments of interest (like bifurcation and a stenosis jet) with the help of suitable thresholds for PSV and spectral broadening. The present invention uses this information to detect the segments of interest without any imaging of the carotid artery. Further, the present invention provides an automated method to characterize the turbulence present in the carotid cluster with differentiated degrees of stenosis. Experimental results have shown this estimation of stenosis in a segment of interest, together with a combination of turbulence with peak systolic velocity, provide a robust technique for evaluating stenosis.

Spectral Doppler ultrasound velocimetry involves the systematic analysis of the spectrum of frequencies that constitute the Doppler signal. The Doppler signal obtained for clinical use is composed of a range of frequencies with varying amplitude content. Therefore, systematic processing is required before the Doppler shift frequencies are computed. The systematic process of FIG. 9 estimates the two most important parameters to be estimated for stenosis evaluation, the PSV and turbulence.

Figure 9:
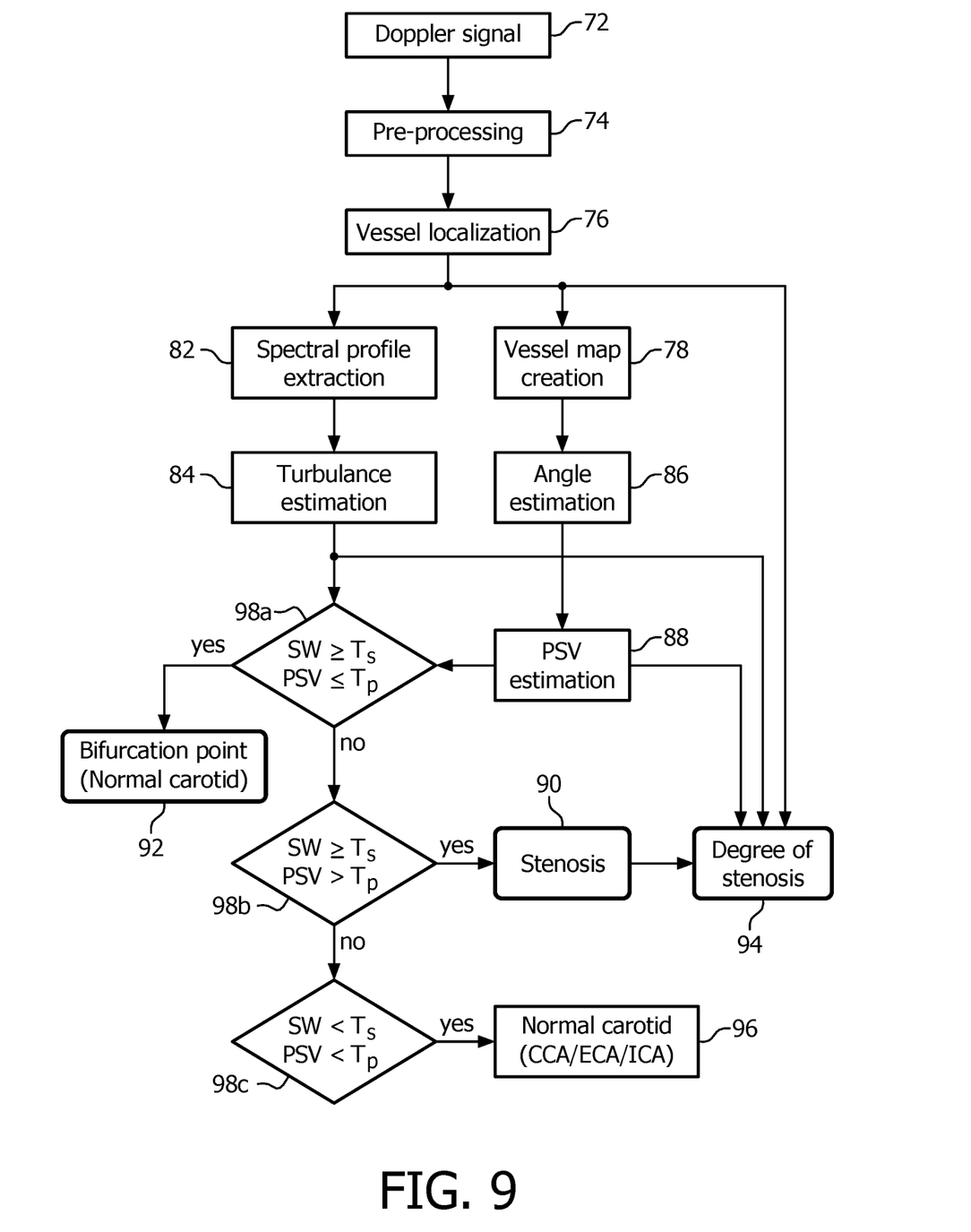
FIG. 9 is a flow chart of the automated assessment of turbulence and peak systolic velocity in a system of the present invention.

In block 72 Doppler signals are acquired from the volumetric region of the carotid artery as described above and the Doppler signals is pre-processed (74) to remove unwanted noisy signal components. The vessel localization step 76 identifies whether the acquired Doppler signals contain vessel information (CCA, ICA, ECA or bifurcation point) or not. This is done with the help of a predefined power threshold for the Doppler power. The power in the time domain (the sum of the square of all the values divided by signal length) is computed for all of the sample volumes of the carotid artery. Then the average power is computed from all the sample volumes. Finally the sample volume that exhibits the highest power above the average value is considered as a segment having vessel information.

The spectral profile extraction at step 82 involves two steps: (i) computing a spectrogram using the spectral Doppler processor 32 and (ii) processing the spectrogram (smoothing, thresholding, noise removal, etc.,) to obtain a good spectral profile. The spectrogram is obtained using a Fast Fourier Transform (FFT) based power spectrum with a 20 millisecond Hamming window using 256 data points and 50% overlap. After this a smooth and reproducible maximum frequency envelope is extracted from the generated spectrogram. To obtain a high quality maximum frequency envelop a first order Infinite Impulse Response (IIR) filter is initially applied to the obtained spectrogram. Next, a 2D median filter is applied to the pulse waveform obtained from the IIR filter. The output of the median filter is used to extract the spectral frequency envelope.

To estimate PSV in step 88, first a 3D vessel map is created in step 78 from the identified vessel information as described previously. From the vessel map the Doppler angle is estimated in step 86 by piecewise linear fit of the geometrical centroids of the carotid vessel structure obtained from the vessel map. The maximum Doppler shift frequency is also computed from the estimated spectral profile.

The peak systolic velocity is estimated in step 88 from the Doppler angle and the maximum Doppler shift using the standard Doppler equation $$v=(F_s \times c)/(2\times F_t \times \cos\theta),$$

where $F_s$ is the Doppler frequency shift, c is the speed of sound in body (assumed to be nominally 1540 m/s), $F_t$ is the frequency of the incident beam and $\theta$ is the angle of beam incidence to the flow direction.

Figure 10:
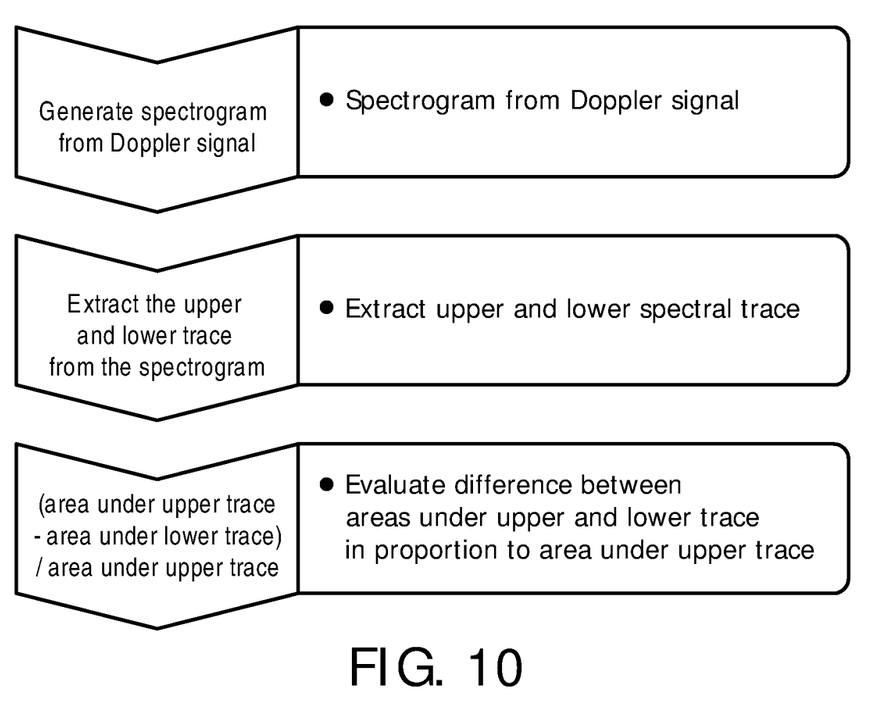
FIG. 10 is a diagram of the basic steps of flow analysis in accordance with the present invention.
Figure 11:
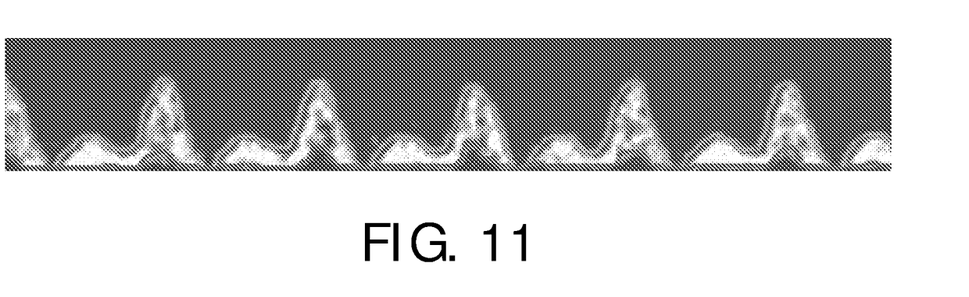
FIG. 11 illustrates a Doppler spectrum with the upper and lower extremes of its envelope traced.

The turbulence is characterized by the spectral broadening which is normally seen in the presence of high flow velocity at the branching of a vessel or in small-diameter vessels. Spectral broadening can be estimated by estimating the bandwidth of the spectrum, also referred to as the spectral width. Turbulence is characterized by estimating the spectral width and therefore extracting both an upper and a lower trace of the envelope of the spectrogram. In an implementation of the present invention, the turbulence was estimated by using the area between the upper and lower spectral traces as a proportion of the area under the upper spectral trace as described by FIG. 10. This drawing illustrates the computation steps involved and an illustration of a traced Doppler spectrogram is shown in FIG. 11. This criterion has the added advantage of placing the three arteries, the common, internal and external carotid, on an equal footing with respect to their peaks. It negates the effect of peak height on the estimate of spectral width. If only the width between the upper and lower envelope traces is used, this can lead to erroneous estimates owing to the external and common carotid having higher peaks than the internal carotid. Accordingly, turbulence is estimated by:

$$\text{Turbulence Criterion} = \frac{\text{Area Under Upper Trace} - \text{Area Under Lower trace}}{\text{Area Under Upper trace}}$$

The concluding determinations of the method of FIG. 9 are to report the finding of the carotid bifurcation point (92), indication of stenosis (90), or a normal carotid (96) to the user. These determinations are made by comparing the turbulence estimate of spectral width SW from step 84 and the PSV estimate from step 88 to a turbulence threshold $T_s$ and a velocity threshold $T_p$ in comparison steps 98a, 98b, and 98c. A nominal velocity threshold $T_p$ is 125 cm/sec, and a nominal turbulence criteria is 0.5. The results of these comparisons are then presented to the user on the display screen.

In summary, an implementation of the present invention provides a method for detecting and characterizing the segments of interest in a carotid artery without any imaging of the vessel. The inventive technique makes use of the non-imaging two dimensional array Doppler probe described above and the method of vessel localization previously described, together with Doppler angle estimation for detecting a stenosis and estimating its severity. Major elements of the invention include computing the turbulence at various points in the carotid structure and characterizing turbulence with differentiated degrees of stenosis; combining the estimates of turbulence and PSV to identify the segments of interest in a carotid artery; and combining the turbulence and PSV estimates to automatically characterize the stenosis of vessel segments in terms of the degree of stenosis.

What is claimed is:
1. A method for aligning spatially different sub-volumes of ultrasonic data of a blood vessel acquired in a single sweep of a probe comprising a two dimensional array of unfocused ultrasonic transducer elements, the method comprising:
   actuating, with a beamformer, each of the unfocused ultrasonic transducer elements to transmit ultrasound waves into a body including a blood vessel;
   receiving, at each of the unfocused ultrasonic transducer elements, temporally spaced echo signals of the blood vessel in a first sub-volume from spatially different depths of scanning, respectively, wherein the array is located in a first position with respect to the blood vessel during the receiving of the temporally spaced echo signals of the blood vessel in the first sub-volume, wherein the temporally spaced echo signals are responsive to the ultrasound waves;
   processing, by a quadrature bandpass filter, the temporally spaced echo signals into quadrature I and Q components,
   estimating, by a Doppler angle estimator, a frequency shift of a Doppler signal at a respective scanning depth in front of each of the unfocused ultrasonic transducer elements based on the quadrature I and Q components, wherein the frequency shift is mapped to a velocity value of flow at the respective scanning depth:
   Doppler processing the temporally spaced echo signals of the blood vessel in the first sub-volume to produce first Doppler data of the scanning depths in the first sub- volume based on the frequency shift of the Doppler signal of each of the unfocused ultrasonic transducer elements;

producing a first three dimensional display map of the first Doppler data in spatial relationship to the first position of the array with respect to the blood vessel in the first sub-volume;

moving the array to a second position with respect to the blood vessel;

actuating, with the beamformer, each of the unfocused ultrasonic transducer elements to transmit second ultrasound waves into the body;

receiving, at each of the unfocused transducer elements, temporally spaced echo signals of the blood vessel responsive to the second ultrasound waves in a second sub-volume from spatially different depths of scanning, respectively, wherein the second sub-volume is spatially different from the first sub-volume, wherein the array is located in the second position with respect to the blood vessel during the receiving of the temporally spaced echo signals of the blood vessel in the second sub-volume, and wherein the second sub-volume partially overlaps the first sub-volume in a first overlapping region;

Doppler processing the temporally spaced echo signals of the blood vessel in the second sub-volume to produce second Doppler data of the scanning depths in the second sub-volume based on the frequency shift of the Doppler signal of each of the unfocused ultrasonic transducer elements; producing a second three dimensional display map of the second Doppler data in spatial relationship to the second position of the array with respect to the blood vessel in the second sub- volume, wherein each of the first and second three dimensional display maps comprises a plurality of columns of voxels extending in a depth direction in front of each transducer element, wherein each column of voxels of the plurality of columns of voxels corresponds to a signal received by a corresponding single unfocused ultrasonic transducer element of the unfocused ultrasonic transducer elements in the array;

aligning the first three dimensional display map and the second three dimensional display map purely based on matching at least a portion of the first and second Doppler data of the first and second three dimensional display maps, wherein a matching portion of the first and second Doppler data are in the first overlapping region, wherein the matching portion of the first and second Doppler data consists of spectral Doppler data; am!

producing a combined three-dimensional display map of blood flow in the blood vessel by stitching together the aligned first and second three-dimensional display maps; and computing accumulated Doppler power of a sum of the signal received by each of the unfocused ultrasonic transducer elements: and providing feedback based on the accumulated Doppler power through a plurality of indicators on a screen.

2. The method of claim 1, further comprising:

moving the array to a third position with respect to the blood vessel, and receiving temporally spaced echo signals of the blood vessel in a third sub-volume, spatially different from the second sub-volume, wherein the array is located in the third position with respect to the blood vessel during the receiving, and wherein the third sub-volume partially overlaps the second sub-volume in a second overlapping region;

Doppler processing the temporally spaced echo signals of the blood vessel in the third sub-volume to produce third Doppler data of scanning depths in the third sub-volume, acquired by each of the transducer elements;

producing a third three dimensional display map of the third Doppler data in spatial relationship to the third position of the array with respect to the blood vessel in the third sub-volume;

aligning the third three dimensional display map with at least the second three dimensional display map purely based on matching at least a portion of the second and third Doppler data of the second and third three dimensional display maps, wherein the portion of the second and third Doppler data are in the second overlapping region; and further producing the combined three dimensional display map by stitching together the aligned second and three dimensional display maps.

3. The method of claim 1, wherein the first and second Doppler data comprise time domain Doppler data.

4. The method of claim 3, wherein the time domain Doppler data comprises peak systolic velocity data.

5. The method of claim 1, further comprising interpolating or smoothing the aligned first and second three dimensional display maps.

6. A system for aligning spatially different sub-volumes of ultrasonic data of a blood vessel, comprising:

a two dimensional array of unfocused ultrasonic transducer elements for receiving at each of the transducer elements, when located at a first position, temporally spaced first echo signals of a blood vessel in a first sub-volume from spatially different depths of scanning, respectively, and for receiving at each of the unfocused ultrasonic transducer elements, when located at a second position different from the first position, temporally spaced second echo signals of the blood vessel in a second sub-volume from spatially different depths of scanning, respectively, wherein the second sub-volume is spatially different from the first sub-volume, and wherein the second sub-volume partially overlaps the first sub-volume in a first overlapping region;

a beamformer for actuating each of the unfocused ultrasonic transducer elements to transmit ultrasound waves into the body to generate the first echo signals and the second echo signals; and at least one processor for executing instructions, stored on one or more non-transitory computer readable media, causing the at least one processor to perform a process comprising:

Doppler processing the first echo signals to produce first Doppler data of the scanning depths in the first sub-volume;

producing a first three dimensional display map of the first Doppler data in spatial relationship to the first position of the array with respect to the blood vessel in the first sub-volume;

Doppler processing the second echo signals to produce second Doppler data of the scanning depths in the second sub-volume;

producing a second three dimensional display map of the second Doppler data in spatial relationship to the second position of the array with respect to the blood vessel in the second sub-volume, wherein each of the first and second three dimensional display maps comprises a plurality of columns of voxels extending in a depth direction in front of each transducer element, each column of voxels of the plurality of columns of voxels corresponds to a signal received by a corresponding single unfocused ultrasonic transducer element of the unfocused ultrasonic transducer elements in the array;

aligning the first three dimensional display map and the second three dimensional display map purely based on matching at least a portion of the first and second Doppler data of the first and second three dimensional display maps, wherein a matching portion of the first and second Doppler data are in the first overlapping region, wherein the matching portion of the first and second Doppler data consists of spectral Doppler data;

stitching together the aligned first and second three dimensional display maps to produce a combined three dimensional display map of blood flow in the blood vessel based on the aligning;

computing accumulated Doppler power of a sum of the signal received by each of the unfocused ultrasonic transducer elements; and providing feedback based on the accumulated Doppler power through a plurality of indicators on a screen.

7. The system of claim 6, wherein the first and second Doppler data comprise time domain Doppler data including peak systolic velocity data.

8. The system of claim 6, wherein each column of voxels comprises a Doppler flow value.

9. The system of claim 6, further comprising interpolating or smoothing the aligned first and second three dimensional display maps.

10. The system of claim 6, wherein each voxel of a column of voxels of the plurality of columns of voxels is generated by depth-gating the first Doppler data or the second Doppler data.

11. A non-transitory computer readable medium storing a computer program for aligning spatially different sub-volumes of ultrasonic data of a blood vessel acquired by a probe comprising a two dimensional array of unfocused ultrasonic transducer elements that are actuated by a beamformer to generate ultrasound waves and in response to the ultrasound waves, the unfocused ultrasonic transducer elements receive, when located at a first position, temporally spaced first echo signals of a blood vessel in a first sub-volume from spatially different depths of scanning, respectively, and that receive, when located at a second position different from the first position, temporally spaced second echo signals of the blood vessel in a second sub-volume from spatially different depths of scanning, respectively, wherein the second sub-volume is spatially different from the first sub-volume, and partially overlaps the first sub-volume in a first overlapping region, when executed by at least one processor, causing the at least one processor to perform a method comprising:

Doppler processing the first echo signals to produce first Doppler data of the scanning depths in the first sub-volume;

producing a first three dimensional display map of the first Doppler data in spatial relationship to the first position of the array with respect to the blood vessel in the first sub-volume;

Doppler processing the second echo signals to produce second Doppler data of the scanning depths in the second sub-volume;

producing a second three dimensional display map of the second Doppler data in spatial relationship to the second position of the array with respect to the blood vessel in the second sub-volume, wherein each of the first and second three dimensional display maps comprises a plurality of columns of voxels extending in the depth dimension in front of each transducer element;

aligning the first three dimensional display map and the second three dimensional display map purely based on matching at least a portion of the first and second Doppler data of the first and second three dimensional display maps, wherein a matching portion of the first and second Doppler data are in the first overlapping region, wherein the matching portion of the first and second Doppler data consists of spectral Doppler data; and stitching together the aligned first and second three dimensional display maps to produce a combined three dimensional display map of blood flow in the blood vessel;

computing accumulated Doppler power of a sum of the signal received by each of the unfocused ultrasonic transducer elements: and providing feedback based on the accumulated Doppler power through a plurality of indicators on a screen.

12. The non-transitory computer readable medium of claim 11, wherein each voxel of a column of voxels of the plurality of columns of voxels is generated by depth-gating the first Doppler data or the second Doppler data.

13. The non-transitory computer readable medium of claim 11, wherein each column of voxels of the plurality of columns of voxels corresponds to a signal received by a corresponding single unfocused ultrasonic transducer element of the unfocused ultrasonic transducer elements in the array.

* * * * *